United States Patent [19]

Miller

[11] Patent Number: 5,236,454
[45] Date of Patent: Aug. 17, 1993

[54] STACKED BREAST IMPLANT

[76] Inventor: Archibald S. Miller, 1145 S. Utica, Ste. 514, Tulsa, Okla. 74104

[21] Appl. No.: 787,679

[22] Filed: Nov. 4, 1991

[51] Int. Cl.⁵ .............................................. A61F 2/12
[52] U.S. Cl. ............................................................ 623/8
[58] Field of Search .................................. 623/7, 8, 66

[56] References Cited

U.S. PATENT DOCUMENTS

| | | | |
|---|---|---|---|
| 3,665,520 | 5/1972 | Perras et al. | 623/8 |
| 3,681,787 | 8/1972 | Perras | 623/8 |
| 3,683,424 | 8/1972 | Pangman | 623/8 |
| 3,883,902 | 5/1975 | Lynch | 623/8 |
| 3,919,724 | 11/1975 | Sanders et al. | 623/8 |
| 4,095,295 | 6/1978 | Lake | 623/8 |
| 4,298,998 | 11/1981 | Naficy | 623/8 |
| 4,428,082 | 1/1984 | Naficy | 623/8 |
| 4,433,440 | 2/1984 | Cohen | 623/8 |
| 4,455,691 | 6/1984 | Van Ahen Redinger et al. | 623/8 |
| 4,472,226 | 9/1984 | Redinger et al. | 623/8 |
| 4,507,810 | 4/1985 | Bartholdson | 623/8 |
| 4,573,999 | 3/1986 | Netto | 623/8 |
| 4,605,412 | 8/1986 | LaForest et al. | 623/8 |
| 4,772,284 | 9/1988 | Jefferies et al. | 623/8 |
| 4,778,465 | 10/1988 | Wilkins | 623/8 |
| 4,790,848 | 12/1988 | Cronin | 623/8 |
| 4,950,292 | 8/1990 | Audretsch | 623/8 |
| 5,035,249 | 7/1991 | Sasaki et al. | 623/8 |
| 5,092,882 | 3/1992 | Lynn et al. | 623/8 |
| 5,116,370 | 5/1992 | Foglietti | 623/8 |
| 5,146,933 | 9/1992 | Boyd | 623/8 |
| 5,147,398 | 9/1992 | Lynn et al. | 623/8 |

FOREIGN PATENT DOCUMENTS

| | | | |
|---|---|---|---|
| 0197726 | 10/1986 | European Pat. Off. | 623/8 |
| 2199266 | 4/1974 | France | 623/8 |

Primary Examiner—Randall L. Green
Assistant Examiner—Gina M. Gualtieri
Attorney, Agent, or Firm—Head & Johnson

[57] ABSTRACT

An implantable stacked breast prosthesis comprising two or more separate chambers stacked on each other, and fastened together eccentrically, so as to give a normal contour to the reconstructed or augmented breast and to prevent slippage of the chambers. At least one of the chambers is collapsed and may be variably filled with liquid.

8 Claims, 3 Drawing Sheets

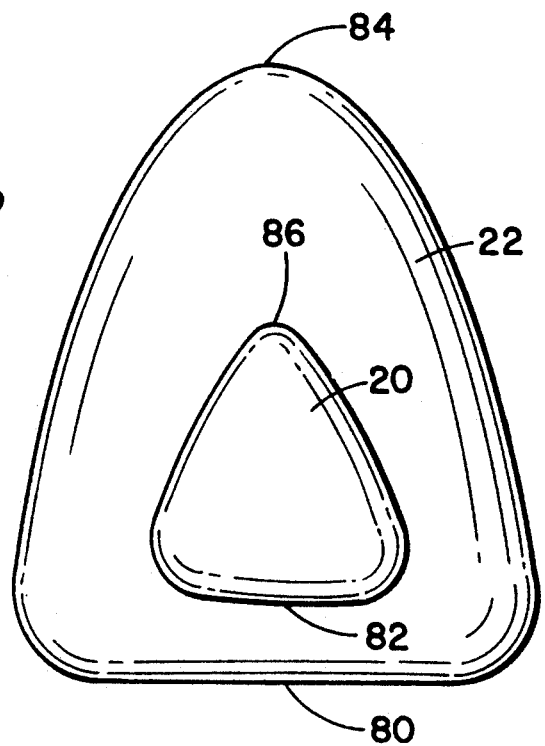
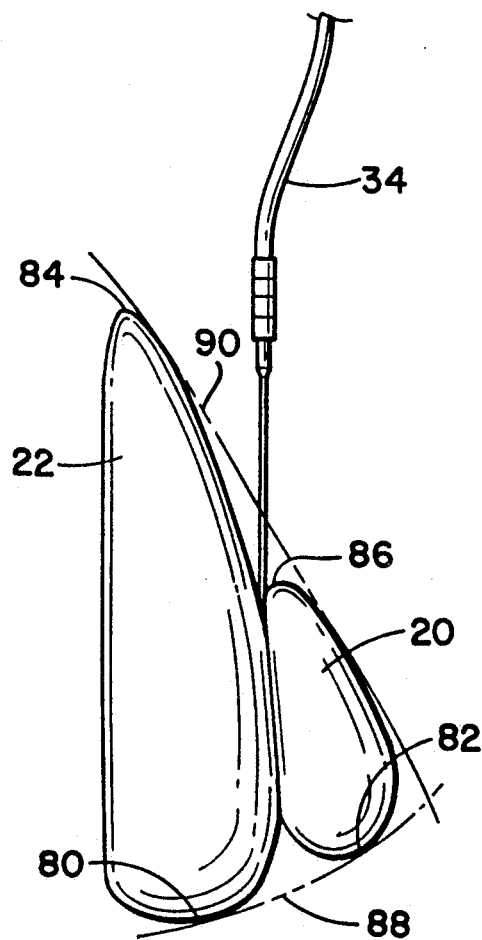

STACKED BREAST IMPLANT

BACKGROUND OF THE INVENTION

1. Field of the Invention

This invention relates in general to the field of implantable breast prostheses, and more particularly to those breast prostheses which are stacked.

2. Description of the related art

Implantable breast prostheses are used primarily in two ways:

1. Augmentation implants: augmentation mammoplasty is used to modify the size and/or shape of an intact breast.

2. Reconstructive implants: reconstructive mammoplasty is used to restructure the area in which a breast has been previously removed or modified.

Various types of implants have been used. In early attempts at breast modification simple injections of material directly into the breast parenchyma was sometimes attempted. This generally was not successful because the injected material would disperse or could not be contoured to give the desired shapes.

Later attempts used discrete implants, usually a single chamber implant filled with a silicone product (see: 3,665,520; 3,681,787; 4,455,691; 4,472,226; 4,573,999; 4,772,284). A problem with this type of implant is that they generally come in one size, can not be individually contoured to the individual patent, they may not give a normal contour to the modified breast, and they require relatively large incisions to insert them. Some implants do have a contoured or irregular shape, but these usually have a single chamber and when suspended in the human breast these tend to deform with most of the filling material pulling the prosthesis down into a pendulous or pear-shape, and these still usually require a large incision. If rigid shapes are used, then the implant gives the breast an abnormal texture or feeling and are difficult to insert and require large incisions.

Some prostheses have used multiple chambers (see 4,507,810 with multiple intercommunicating chambers). Many of these do not impart a normal contour to the reconstructed or augmented breast. These cannot be adjusted or "customized" for the individual recipient, and they may require large incisions.

Recently, some surgeons have used "stacked" implants. These generally consist of two implants stacked upon each other as needed in the mammoplasty process. However, there has been a problem with this type of implant procedure since the stacked implants tend to drift apart. Also, they may turn in relation to each other and in relation to the breast and they cannot be kept in an eccentric position relative to each other.

SUMMARY OF THE INVENTION

It is an object of this invention to provide a stacked implant with the various stacked elements attached to each other.

It is also an object of this invention to attach the stacked elements in an eccentric manner, so as to more closely approximate the contour of a normal breast.

It is another object of this invention to provide a stacked implant with means for securing the implant to the breast tissues so that it will not turn or slip.

It is a further object of this invention to provide a stacked implant with two, or more, separate implant elements attached to each other.

It is yet another object of this invention to provide a stacked implant in which at least one of the implant elements is variably fillable with liquid or other filling material.

It is another object of this invention to provide a stacked implant that may be inserted into the breast through a relatively small incision.

A further object is to provide an implant that will impart an essentially normal contour to the human breast after implantation.

Another object is to provide an implant that will provide an "normal" texture and feel to the breast after it is implanted.

It is yet a further object of this invention to provide an implant that may be individualized or customized by the surgeon for each patient.

It is also an object of this invention to provide a method for making stacked implants and for using stacked implants in the human breast.

In the preferred embodiment the stacked implant is comprised of two discoid or lenticular shaped implant elements; more than two elements may be used. The bottom element is applied next to the chest wall, and the top element is mounted (stacked) eccentrically on top of the bottom element, with adhesive or other suitable attaching means. The stacking of the elements, and their individual shapes, are optimized to give a normal appearance and contour to the reconstructed or augmented breast. The bottom element has a volume that is about twice that of the top element. The top element has a valve for injecting saline after insertion. The bottom element may have peripheral tabs for attaching the implant to the breast tissues. The top element is deflated when inserted, thereby allowing the implant to be inserted through a smaller incision, and is variably inflated with saline or other fluid, after insertion and placement, thus allowing customization by varying the amount injected.

These objects are meant to be illustrative and not limiting. The manner of operation, novel features and further objectives and advantages of this invention may be better understood by reference to the accompanying drawings, description and claims.

BRIEF DESCRIPTION OF THE DRAWINGS

FIG. 8 is a frontal view of two stacked implants with "tear-drop" or "triangular" shapes.

FIG. 9 is a side-view of the stacked "tear-drop" shaped implants.

DESCRIPTION OF THE PREFERRED EMBODIMENT

Figure 1:
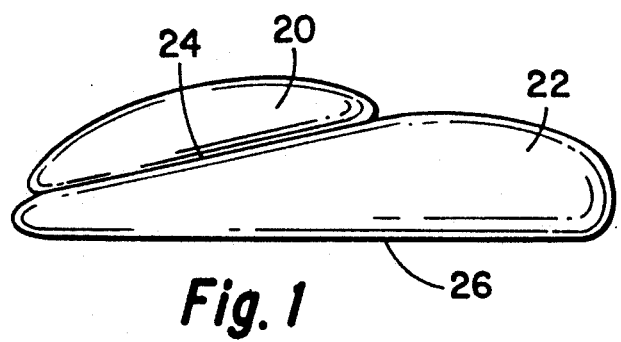
FIG. 1 is a side-view of a two element stacked implant.

FIG. 1 illustrates a cross-section of a stacked implant with two implant elements. A top implant element 20 is mounted eccentrically on a bottom implant element 22. These are discoid or lenticulate in shape, and the bottom implant element 22 has a volume approximately twice that of the top implant element 20 (2:1 bottom:top). It is preferred that the shape of the elements be more lenticulate with downward sloping edges (as illustrated) which gives a smoother contour, and a more natural outline to the breast when implanted therein. The area of attachment of the two implant elements, generally indicated by 24, is eccentric on the bottom implant element 22. The bottom surface, generally indicated by 26, of the bottom implant element 22, is placed approximately parallel to, and adjacent to, the chest wall when inserted (see FIGS. 6 and 7 below).

Figure 2:
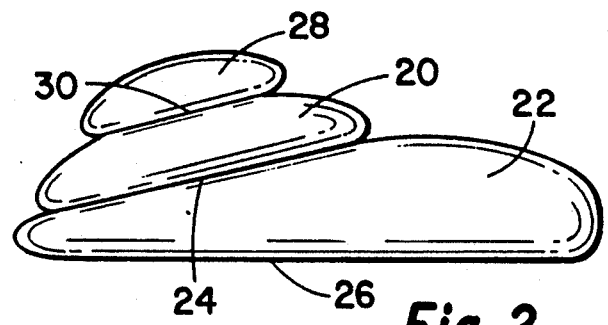
FIG. 2 is a side-view of a three element stacked implant.

FIG. 2 illustrates a cross-section of a stacked implant with three implant elements. This is similar to FIG. 1, but with a third implant element 28, attached to the top of implant element 20. The ratio of volume is about 1:2:4 (top:middle:bottom). Implant element 28 is eccentrically attached to implant element 20, generally indicated at 30.

In the preferred two implant element embodiment the bottom implant element 22 is filled with a silicone gel, and the top element 20 is collapsed for ease of surgical insertion, and then filled with saline after insertion into the breast. This allows the implant to be inserted through a smaller incision. It also allows the surgeon, by varying the amount of saline injected, to individualize and customize the implant to each patient. If more than two implant elements are used, all elements, except the bottom element, may be collapsed prior to insertion.

Figure 3:
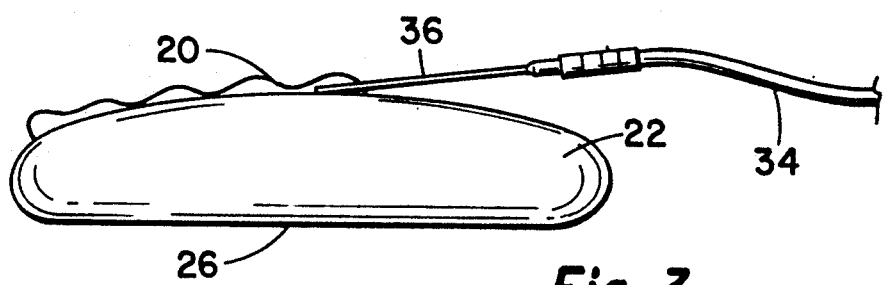
FIG. 3 is a side-view of a two element stacked implant with the top element collapsed, and with injection apparatus in place.

FIG. 3 illustrates the two implant element embodiment with the top implant element 20 collapsed, and eccentrically mounted on the bottom implant element 22. Tubing 34 attached to a cannula 36 is present through which saline, or other filling material, may be injected into the top implant element 20 after inserting the implant into the patient. The bottom implant element 22 may also be filled with saline, collagen, or other suitable materials other than silicone gel.

The walls and structure of the implants may be made of any suitable biocompatible material. Preferably, the walls are of an elastomeric material, and there is a lumen within each implant element. I have found that using a bottom element 22 made by Dow Corning Wright using their SILASTIC® MSI implant and the top element 20 made of their silicone elastomer envelope material, works well. U.S. Pat. Nos. 4,455,691 and 4,472,226 are exemplary of some of these types of materials. The two implant elements 20 and 22 are attached eccentrically 24, as noted above. In the current embodiment that I have tested, these are attached using an adhesive, and prefabricated and attached by the manufacturer. However, other methods of attachment may be used, such as clips, snaps, VELCRO®, or the like. Some of the latter mentioned means of attachment allow the surgeon to attach, detach, or rearrange the stacked implant at the time of use as necessary for each patient. Attachment may also be accomplished by heat welding together, by using solvents that caused the implants elements to stick together, by forming the two (or more) implant elements as joined structures in the manufacturing process, or by other suitable means.

Figure 4:
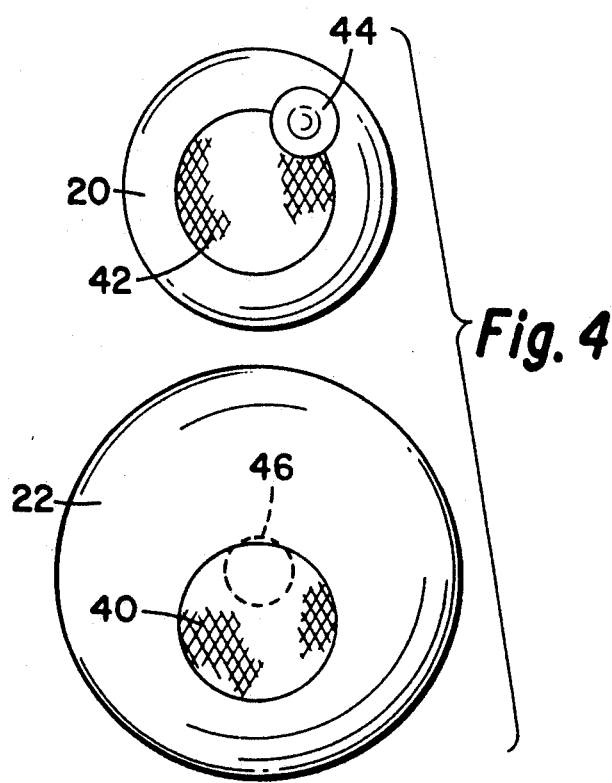
FIG. 4 is an exploded view of a two element stacked implant, showing valves, and adhesive.

FIG. 4 is an exploded view of the two element implant prosthesis. This shows the bottom of the top element 20 and the top of the bottom element 22, and the shaded areas on each are the areas of adhesive, 42 and 40 respectively, which are applied to each other to attach 20 to 22. Also shown in this view, is the valve 44 through which the top element 20 is filled. This may be a flap-valve, or other suitable resealable type of valve. It is this valve 44 into which the cannula 36, in FIG. 3, is inserted. Also shown in FIG. 4, (in dashed outline) is the valve 46 on the bottom surface 26 of the bottom element 22, through which the bottom element 22 is filled. As mentioned above, the bottom element 22 is pre-filled by the manufacturer in the embodiment that I have tested. But, a collapsible bottom element 22 with a resealable valve 46 may be used, which would give the surgeon more flexibility at the time of operation.

Figure 5:
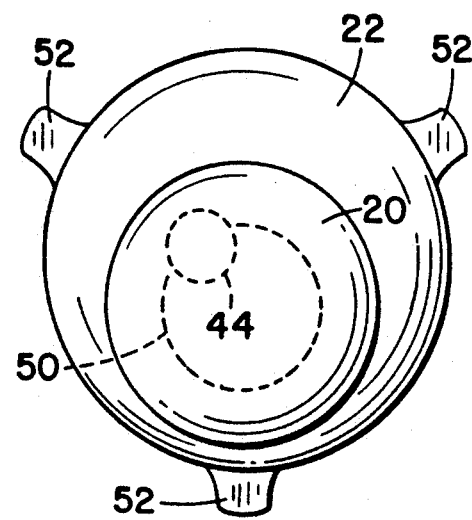
FIG. 5 is a top view of a two element stacked implant, with tabs around the periphery.

FIG. 5 illustrates the two implant element stacked prosthesis with the top implant element 20, bottom implant element 22, valve 44 (in dashed outline) to top element 20, and the area of adhesive application indicated in dashed outline generally at 50. The eccentric positioning of the top implant element 20 in relation to the bottom implant element 22, is illustrated. Also shown in this view are tabs 52 which are attached to the periphery of the bottom element 22, and which may be sewn, or otherwise attached, to tissue in the area of implant to fix the implant in place so that it will not turn or slip. This view illustrates three such tabs 52, but more or less may be used, as necessary.

Figure 6:
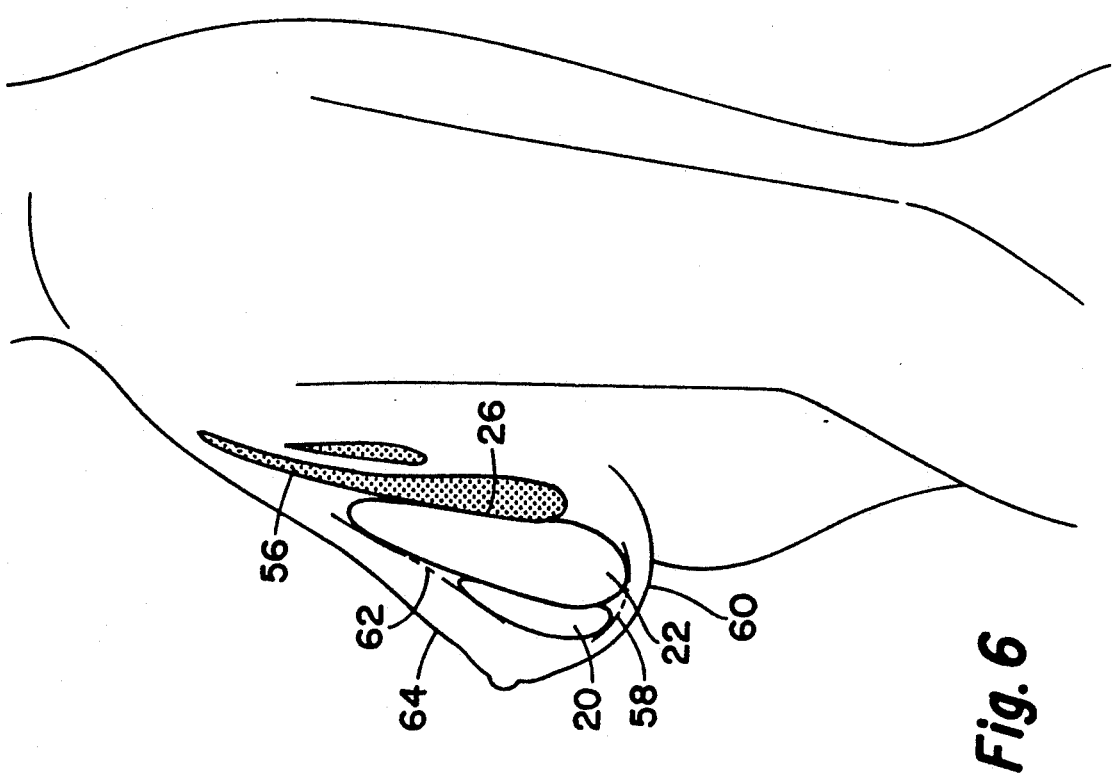
FIG. 6 is a sectional side-view of a human breast with the device used in an augmentation mammoplasty.

FIG. 6 illustrates the two element stacked implant, used as an augmentation implant, in a sectional side-view of a female. In this view the bottom of the implant 26 lies above, and roughly parallel to, the chest muscle 56 (pectoralis major). This view also shows how the lower margin on the top 20 and bottom 22 implant elements forms a smooth contour, generally indicated at 58, which closely approximates the lower curve of the breast, generally indicated at 60. The upper outline of the implant, generally indicated at 62, also approximates the upper curve of the breast 64. The lenticular shapes used give a smooth flowing contour to the stacked implant elements, and the eccentric attachment approximates the normal breast outline. In use, the top implant element 20 is collapsed so the prosthesis may be inserted through a small incision, and then inflated after insertion. Peripheral tabs (as shown in FIG. 5) may be sutured to the breast tissues to keep the prosthesis from turning or slipping.

Figure 7:
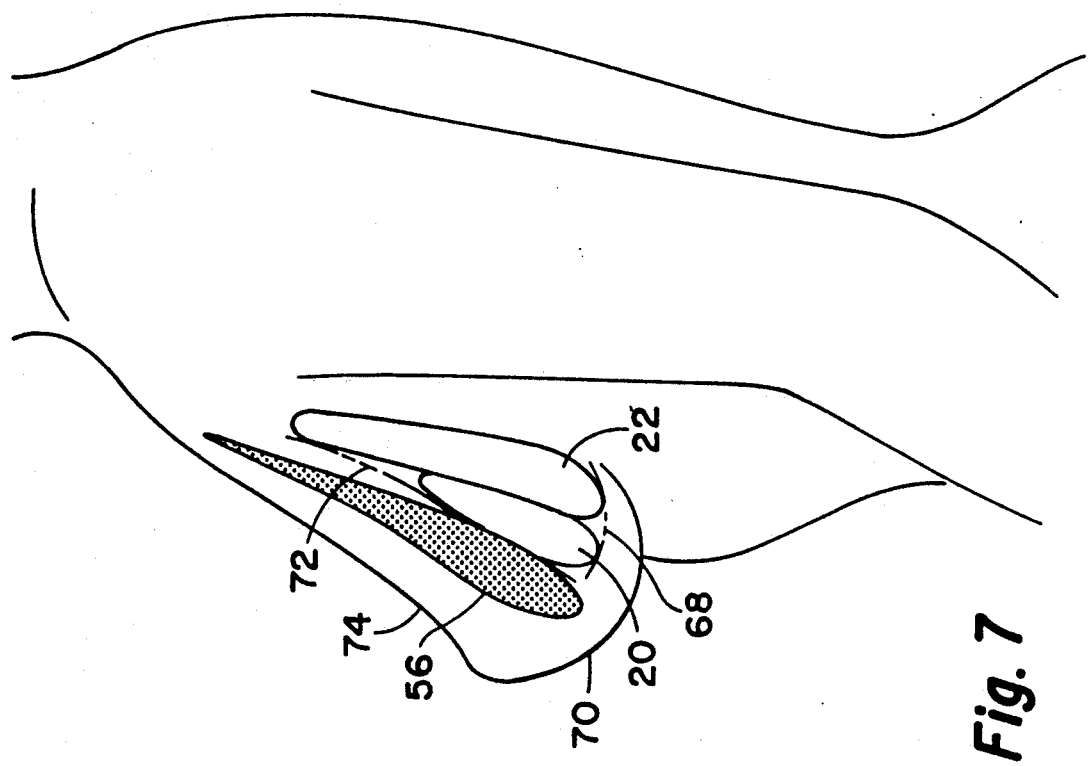
FIG. 7 is a sectional side-view of a human breast with the device used in a reconstructive mammoplasty.

FIG. 7 illustrates the two element stacked implant, used as a reconstructive implant, in a sectional side-view of a female. In this view the bottom contour of the implant, generally indicated at 68, again approximates the lower curve of a normal breast 70. The upper contour of the implant, generally indicated at 72 approximates the upper curve 74 of the normal breast. It is important that the implant give shape and form to the breast in reconstruction, since the bulk of the breast tissue may have been previously removed. In reconstructive use the implant is usually inserted behind the muscle, and there is no nipple.

FIG. 8 illustrates a variation of the implant, in which two implant elements are used, an upper implant element 20 and a lower implant element 22. In this embodiment, the implant elements are "tear-drop" or roughly triangular in shape. This more closely approximates the normal contour of the female breast in frontal view. The two elements 20 and 22 are attached eccentrically. The lower edges and 82 of the implant elements 22 and 20 respectively, are roughly straight, or have a slight curve (these forming the based of the triangle, or head of the "tear-drops"). The top 84 and 86 of the elements 22 and 20 respectively are more sharply curved (these forming the apices of the triangles, or tails of the "tear-drops").

FIG. 9 illustrates the embodiment shown in FIG. 8 in side-view. The lower contour, generally indicated at 88 closely approximates the lower curve of a normal female human breast. Likewise, the frontal profile, generally indicated at 90, closely approximates the anterior curve of the normal human female breast. Filling tubing 34 is also shown.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A permanently implantable stacked breast tissue prosthesis assembly comprising:
    at least two stacked implant envelopes each of which has a shell defining an inner fluid containable chamber and an outer surface to be in direct contact with breast tissue;
    means for eccentrically attaching said outer surface of each of said shell forming said stacked implant envelopes together which form said assembly; and
    at least one resealable valve formed as a part of a wall of at least one of said implant envelopes, means for varying and permanently maintaining the fluid constant of the chamber of said at least one of said implant envelopes whereby once said assembly is implanted in said breast tissue, will achieve and maintain a desired cosmetic shape.

2. The breast prosthesis assembly of claim 1 wherein there are three attached stacked implant envelopes, each having an outer surface and a lumen, comprising:
    a top implant envelope;
    a middle implant envelope;
    a bottom implant envelope;
    said assembly comprising:
        a bottom outer surface of the top implant envelope attached eccentrically to a top outer surface of the middle implant envelope; and
        a bottom outer surface of the middle implant envelope attached eccentrically to a top outer surface of the bottom implant envelope a portion of each of said assembled envelopes to be in direct contact with breast tissue; and
    resealable valves, permanently mounted in the outer surface of each of said implant envelopes, through which the fluid content within the lumen of each of said implant envelopes may be varied.

3. The breast prosthesis of claim 2 wherein said top implant envelope, middle implant envelope nd bottom implant envelope have a volume ratio of approximately 1:2:4 in relation to each other respectively.

4. The breast prosthesis of claim 1 wherein there are two stacked implant envelopes: a top implant envelope and a bottom implant envelope; each of which is lenticular in outline; said bottom implant envelope having a fluid volume approximately twice that of said top implant envelope.

5. The breast prosthesis of claim 4 wherein one or both of said top and bottom implant envelopes includes means to variably adjust said fluid volume therein.

6. A stacked breast prosthesis assembly that is to be implanted into direct contact with tissue of said breast comprising:
    a first implant element comprising:
        a collapsed elastomeric shell defining an outer surface and enclosing an essentially empty lumen; and
        means formed as a part of said outer surface for introducing fluid into said lumen;
    a second collapsed implant element, having a volume approximately twice a volume capacity of the first implant element comprising:
        an elastomeric shell defining an outer surface and enclosing a lumen at least partially filled with a liquid fill compound;
    means for eccentrically attaching a portion of said outer surface of said first implant element to a portion of said outer surface of said second implant element to form said assembly; and
    means for fixing portions of the outer surface of said second implant element directly to said tissues within a breast.

7. The breast prosthesis of claim 6 wherein each of said stacked elements have a "tear-drop" shape.

8. A method for making a stacked breast prosthesis assembly that is to be implanted into direct contact with breast tissue, comprising the steps of:
    forming a first implant element of an elastomeric envelope with an essentially empty shell defining an outer surface to be in direct contact with breast tissue, said envelope having a given volume, and providing as a part of said outer surface a resealable valve means for variably introducing fluid into said shell to achieve a desired cosmetic shape;
    making a second implant element of an elastomeric envelope formed of a shell having an outer surface to be in direct contact with breast tissue, with approximately at least twice the volume of said first implant element, and filing said shell with a liquid fill material,; and
    attaching a portion of the outer surface of said first implant element eccentrically to a portion of the outer surface of said second implant element.

* * * * *